United States Patent [19]

Nishihara

[11] Patent Number: 5,359,512
[45] Date of Patent: Oct. 25, 1994

[54] PICTURE ARCHIVING COMMUNICATION SYSTEM WITH MIGRATION PROCESSING FILE MANAGEMENT FOR MEDICAL APPLICATION

[75] Inventor: Eitaro Nishihara, Ootawara, Japan

[73] Assignee: Kabushiki Kaisha Toshiba, Kawasaki, Japan

[21] Appl. No.: 969,350

[22] Filed: Oct. 30, 1992

[30] Foreign Application Priority Data

Oct. 31, 1991 [JP] Japan ................................ 3-286603

[51] Int. Cl.$^5$ ............................................. G06F 15/42
[52] U.S. Cl. ............................. 364/413.01; 364/413.22
[58] Field of Search ................... 364/413.01, 413.13, 364/413.22, 413.02, 413.14

[56] References Cited

U.S. PATENT DOCUMENTS

| | | |
|---|---|---|
| 4,817,050 | 3/1989 | Komatsu et al. |
| 4,833,625 | 5/1989 | Fisher et al. ................. 364/413.22 |
| 5,001,569 | 3/1991 | Shigyo . |
| 5,018,178 | 5/1991 | Katsumata . |
| 5,019,975 | 5/1991 | Mukai ........................... 364/413.13 |

Primary Examiner—Robert A. Weinhardt
Attorney, Agent, or Firm—Oblon, Spivak, McClelland, Maier & Neustadt

[57] ABSTRACT

A picture archiving communication system for medical application includes least one work station, a data base, including a low-speed recording medium and a high-speed recording medium, for storing image data collected by a diagnosing apparatus unit. When a transfer command for desired image data is sent from the work station to the data base, the image data from the image data registered in the data base is read-out to the work station. A migration processing unit copies image data stored in the low-speed recording medium to the high-speed recording medium in the data base. A file management unit is provided, including a management table for storing a migration index number corresponding to at least one image data in the high-speed recording medium, which was subjected to the migration processing, and including a record indicating whether the image data stored in the high-speed recording medium was accessed after the migration processing. This system may further determine whether the image data stored in the high-speed recording medium from the management table has been accessed, and, if the image data has been accessed, deleting the image data from the high-speed recording medium from the earliest accessed one.

7 Claims, 8 Drawing Sheets

| MIGRATION ID NUMBER | IMAGE ID | |
|---|---|---|
| 001 | #5 | #21 |
| | #3 | #4 |
| | #22 | #6 |
| | ///// | #7 |
| 002 | #23 | #24 |
| | #8 | #9 |
| | #10 | #21 |
| 003 | #101 | #104 |
| | #102 | #105 |
| | #103 | ///// |
| 004 | #1 | #2 |
| | #5 | ///// |
| 005 | #200 | #201 |
| | #202 | #204 |
| | #203 | #205 |

F I G. 6

| IMAGE ID | MAGNETIC DISC DRIVE ADDRESS | OPTICAL DISC DRIVE ADDRESS | MIGRATION ID NUMBER | ACCESS RECORD |
|---|---|---|---|---|
| #1 | 7FE0 | 1024 | 4 | NULL |
| #2 | 7FCD | 1025 | 4 | NULL |
| #3 | NULL | 2048 | NULL | NULL |
| #4 | NULL | 2049 | NULL | NULL |
| #5 | 8077 | 2148 | 4,1 | 1 |
| - | - | - | - | |
| - | - | - | - | |
| - | - | - | - | |
| | | | | |
| - | - | - | - | |
| - | - | - | - | |
| #1048 | #7A00 | 3049 | 7 | 7 |
| #1049 | #7B00 | 4096 | 7 | 7 |

PICTURE ARCHIVING COMMUNICATION SYSTEM WITH MIGRATION PROCESSING FILE MANAGEMENT FOR MEDICAL APPLICATION

BACKGROUND OF THE INVENTION

1. Field of the Invention

The present invention relates to a picture archiving communication system for medical application (hereinafter referred to as "PACS") having a data base for archiving medical images and accompanying data.

2. Description of the Related Art

Figure 1:
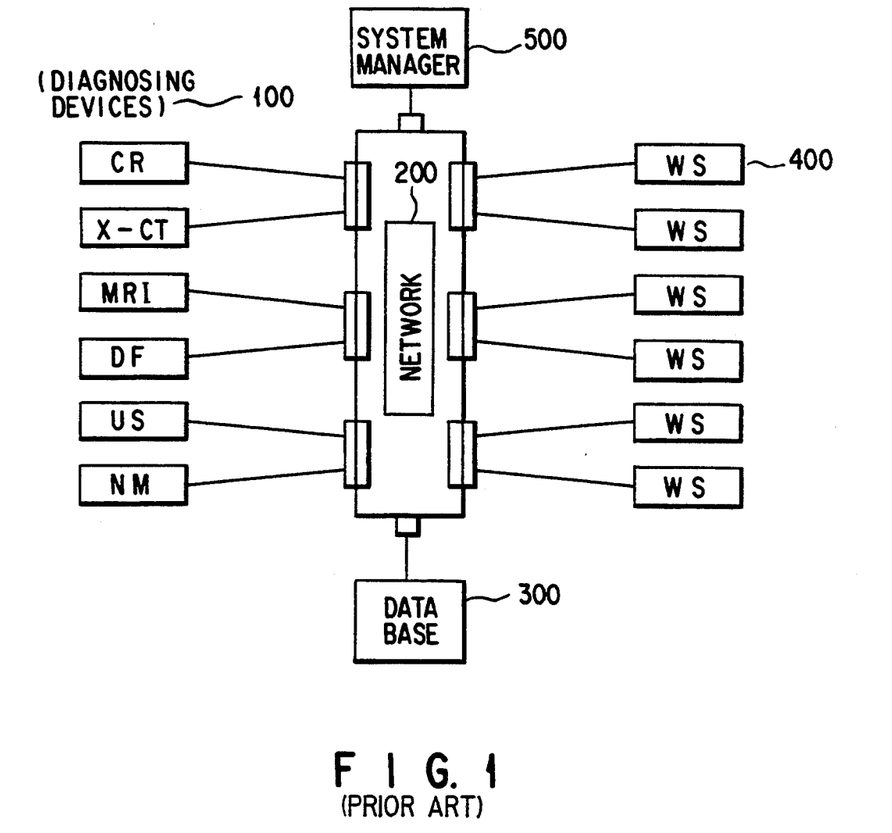
FIG. 1 is the overall structure of a conventional picture archiving communication system for medical application (PACS)

A standard PACS has a structure as shown in FIG. 1. As shown in FIG. 1, diagnosing apparatuses 100 include a CR (Computed Radiography), an X-CT (x-ray tomographic imaging apparatus), an MRI (nuclear magnetic resonance imaging apparatus), a DF (digital fluorography apparatus), a US (ultrasonic diagnosing apparatus) and an NM (nuclear medicine apparatus). Image data collected by the various diagnosing apparatuses 100 is registered in a data base 300 via a network 200. On the other hand, when image data is referred to by work stations 400 (WS) arranged at various locations, a desired image index (ID) (e.g. a number assigned to each image) or an examination index is delivered from the work station 400 to the data base 300 to request transfer of image data. In response to a command from a system manager 500, image data corresponding to the work station 400 (WS) is transferred and displayed on an image display such as a CRT.

Figure 2:
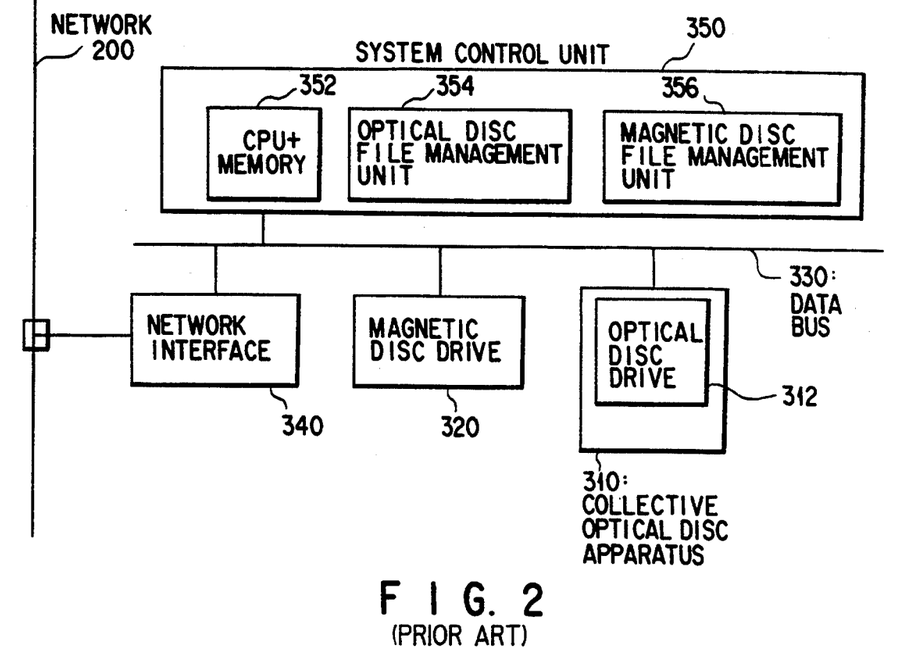
FIG. 2 shows the structure of a conventional data system.

The data base 300 of the PACS, as shown in FIG. 2, comprises a optical disc library 310 having an optical disc drive 312, a magnetic disc drive 320, a system control unit 350, and a network interface 340. These devices are connected to a data bus 330. In this case, the system control 350 comprises a CPU 352 including a memory, an optical disc file management unit 354, and a magnetic disc file management unit 356.

In the data base system having the above structure, image data is normally stored in an optical disc drive 312. If the optical disc library 310 including a plurality of optical disc drives 312 is used, a large quantity of image data can be stored. In this case, however, the access time increases to several-ten seconds. If image data is stored in the magnetic disc drive 320, the access time of image data can be decreased. However, the storage capacity of the magnetic disc drive 320 is lower than the optical disc drive 312.

In general, among image data stored in the optical disc drive 312, image data likely to be accessed in the future (within a few days) is estimated, and such data is copied from the optical disc 312 to the magnetic disc drive 320 in advance. This processing is called "migration processing".

Figure 3:
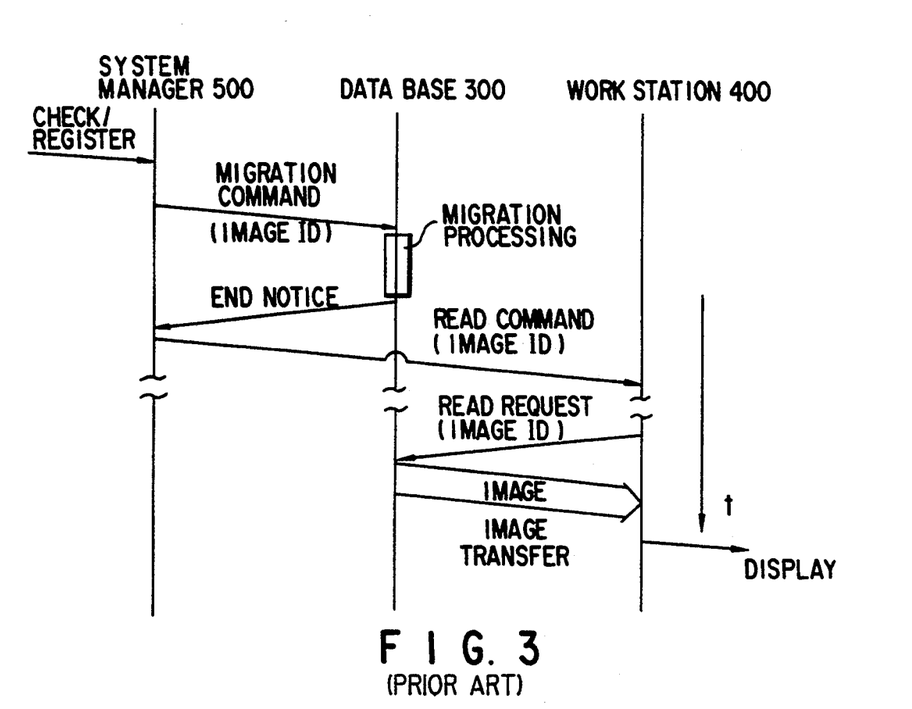
FIG. 3 illustrates the operation of the conventional system in response to commands and requests.

FIG. 3 is a view for explaining the overall operation of the PACS in the "migration processing" mode. Referring to FIG. 3, the system manager 500 supplies at least one image index ("image ID" hereinafter) to the data base 300. The image ID is supplied to the CPU 352 of the system control unit 350 in the database 300 shown in FIG. 2. Then, the system control unit 350 accesses the optical disc file management unit 354 and finds the physical address for the optical disc drive 312, thereby reading out the corresponding image data. Subsequently, the system control unit 350 accesses the magnetic disc file management unit 356 and finds the address to be written, thereby writing image data read out from the optical disc drive 312 at the corresponding address of the magnetic disc drive 320.

Figure 4:
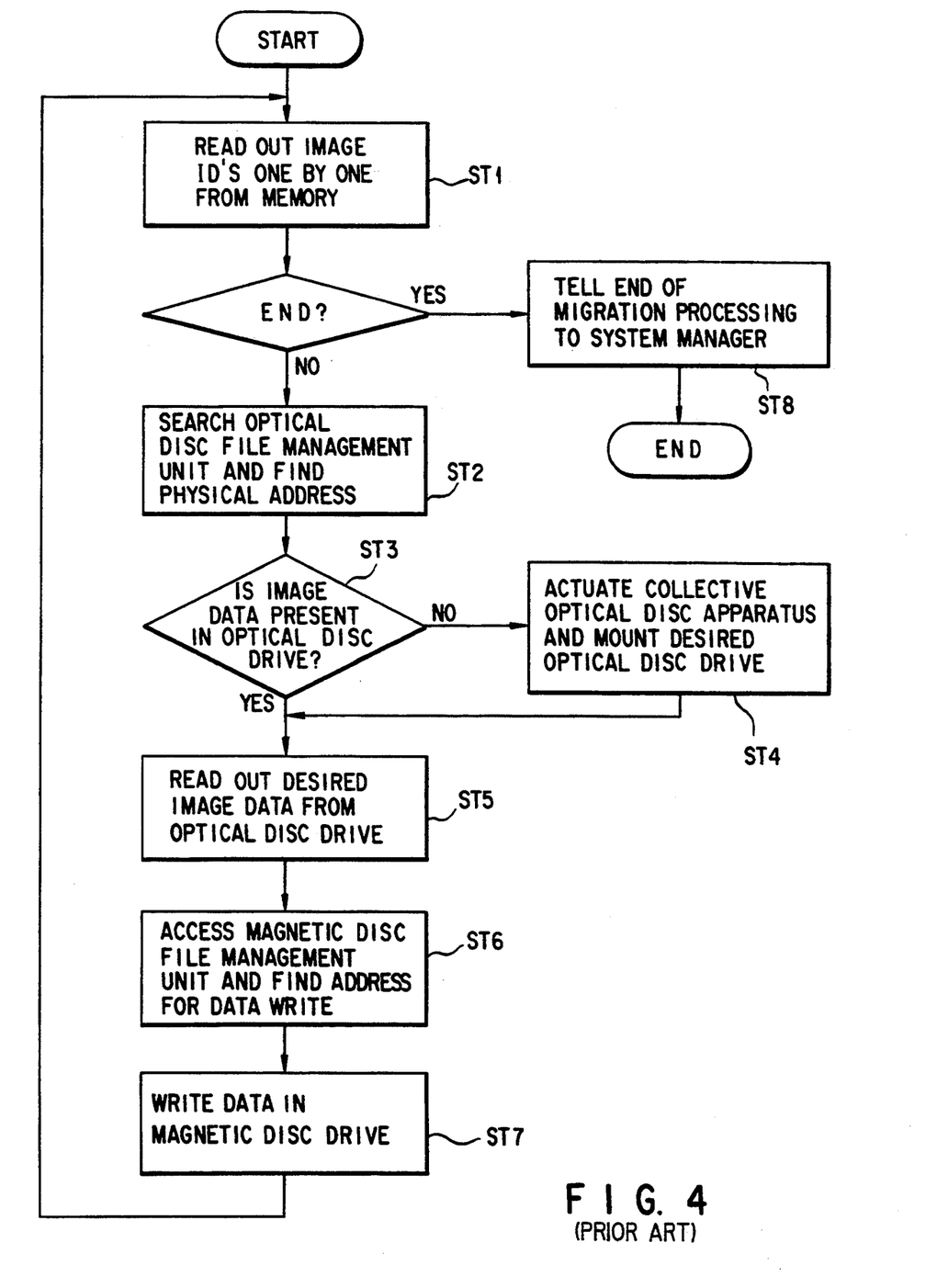
FIG. 4 is a flow chart illustrating the migration processing in the conventional data base.

FIG. 4 is a flow chart showing the migration processing in detail.

When a program is activated by a migration command from the system manager 500, each image ID is read out one by one from the memory provided within the CPU 352 (step ST1).

Then, the optical disc file management unit 354 is accessed, and the physical address associated with the image ID of the optical disc drive 312 is found (step ST2). In step ST3, it is determined whether the image data corresponding to the image ID is present at the address of the optical disc drive 312. If "NO" in step ST3, the arm of the optical disc library 310 is actuated, and a desired optical disc drive 312 is mounted (step ST4). If "YES" in step ST3, or after step ST4, desired image data is read out from the optical disc drive 312 (step ST5) and the control routine goes to step ST6. In step ST6, the magnetic disc file management unit 356 is accessed, and the address for write of desired image data is found. The image data corresponding to the image ID is written at the corresponding address of the magnetic disc drive 320 (step ST7).

Referring to the flow chart of FIG. 4, the processing of one image ID was described. After the steps ST1 to ST7 are completed, the control routine goes back to step ST1, and the same processing is repeated. Once the migration processing for all desired image IDs have been completed, the completion is told to the system manager 500 (step ST8) and the entire processing is finished.

After the end notice of the migration processing is transmitted to the system manager 500, the system manager 500 supplies a command to the work station 400, as shown in FIG. 3, to read out all image IDs which have been subjected to the migration processing. Thereafter, a command for reading the image ID is supplied from the work station 400 to the data base 300. Thus, desired image data is transferred from the magnetic disc drive 320 to the work station 400.

In the PACS with the above data base 300, the capacity of the magnetic disc drive 320 is limited. Thus, it is necessary to delete unnecessary files on an as-needed basis. In this case, the magnetic disc drive 320 stores, in a mixed manner, modalities, data registered by the work station, etc., data read out from the optical disc drive 312 in the migration processing, data used temporarily as buffer, and data for backup of data on the system disc and memory, etc. Accordingly, when data in the magnetic disc drive 320 is deleted, such data is generally deleted by referring to the earliest date of access of files.

However, when data transfer is performed in the data base 300 after a certain period from the migration processing, it is possible that part of a desired file is deleted before the data transfer. The fact of deletion of data is not detected in the system manager 500 or work station 400. Consequently, when data is accessed by the work station 400, desired image data is not in the magnetic disc drive 320 and the optical disc drive 312 must be accessed once again. Thus, the wait time increases considerably.

SUMMARY OF THE INVENTION

The object of the present invention is to provide a picture archiving communication system for medical application (PACS) capable of effectively performing migration processing and increasing the access speed of image data.

According to one aspect of the invention, there is provided a picture archiving communication system for medical application, comprising:

at least one work station;

a data base, including a low-speed recording medium and a high-speed recording medium, for storing image data collected by a diagnosing apparatus;

means for reading out, when a transfer command for desired image data is sent from the work station to the data base, the image data from the image data registered in the data base and transfers the read-out image data to the work station;

migration processing means for performing migration processing in which image data stored in the low-speed recording medium is copied to the high-speed recording medium in the data base; and file management means including a management table for storing a migration index number corresponding to at least one image data in the high-speed recording medium, which was subjected to the migration processing, and a record indicating whether the image data stored in the high-speed recording medium was accessed after the migration processing.

This system may further comprise data deleting means for determining whether the image data stored in the high-speed recording medium from the management table has been accessed, and, if the image data has been accessed, deleting the image data from the high-speed recording medium from the earliest accessed image data.

According to the PACS of this invention, the migrated image data on the high-speed recording medium can preferentially be stored on the management table of the file management means of the data base. Thus, the user can always access data within a predetermined period. Further, since image indexes can collectively be managed for each migration index, the control of the entire system is easy.

In addition, the image data can be deleted from the earliest accessed image file, by referring to the access record (e.g. flag) indicating whether the image data was accessed as header information of the data in the high-speed recording medium. Thus, non-accessed data is not deleted from the high-speed recording medium.

As has been stated above, the present invention can provide a picture archiving communication system for medical application (PACS) capable of effectively performing migration processing and increasing the access speed of image data.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which.

DETAILED DESCRIPTION OF THE PREFERRED EMBODIMENTS

An embodiment of the present invention will now be described with reference to the accompanying drawings.

Figure 5:
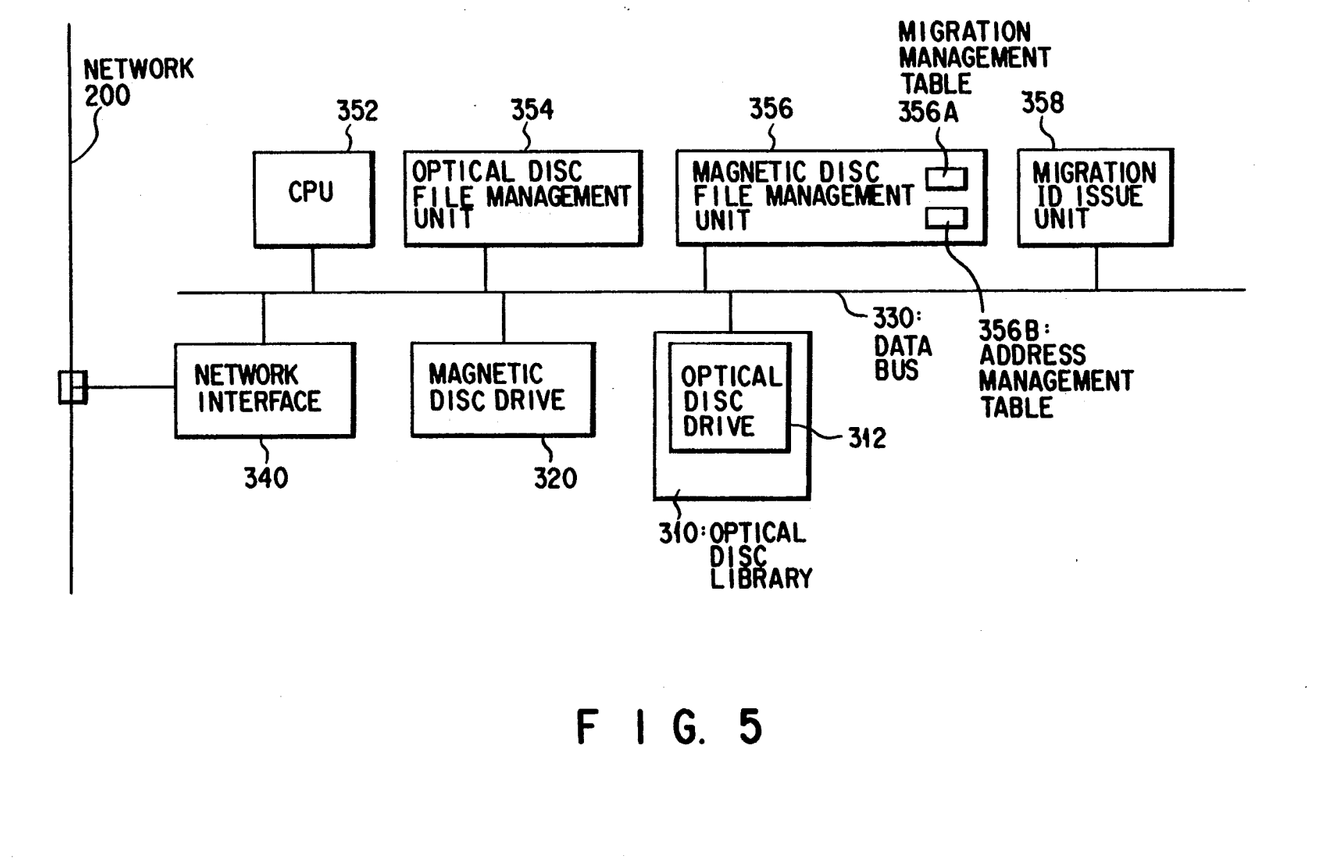
FIG. 5 shows the structure of a data base system of a PACS according to an embodiment of the invention.

FIG. 5 shows the structure of a data base system, according to the present invention, for use in the PACS shown in FIG. 1. In FIG. 5, the same parts as in FIG. 2 are denoted by like reference numerals, and a description thereof is omitted. Only the differences are described. The overall structure of the PACS shown in FIG. 1 is unchanged.

In this embodiment, as shown in FIG. 5, the magnetic disc file management unit 356 is provided with a migration management table 356A and an address management table 356B. A migration index issue unit (migration ID issue unit) 358 is newly provided and connected to the data bus 330.

A unique number in the system may be used as a migration ID number issued by the migration ID issue unit 358. For example, when a migration ID number is issued by the data base system, the migration ID number may be a combination of a data base number assigned to the data base 300 and a sequential number corresponding to the order of issued ID numbers in the data base 300.

Figure 6:
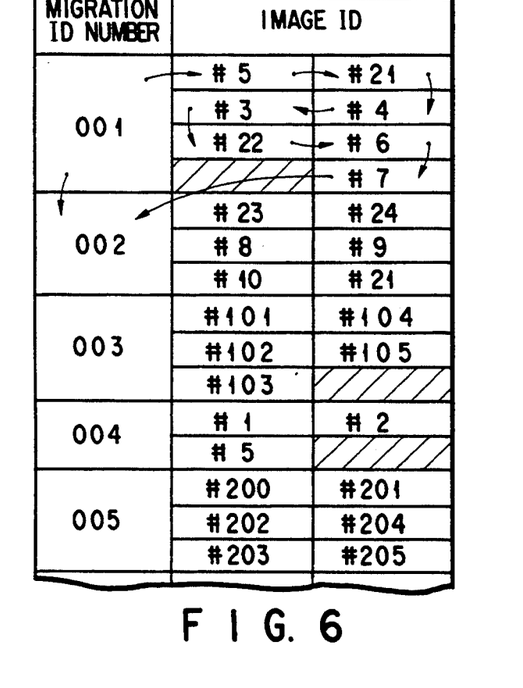
FIG. 6 shows a migration management table according the embodiment.

FIG. 6 shows an example of the migration management table 356A. Image IDs transferred by migration are linked by using migration IDs as keys. Since a migration ID number is linked to the next migration ID number, only the migration ID number can be searched until a desired migration ID number is found. For example, a search can be conducted in a route from migration ID number 001 to migration ID number 002, or in a route from migration ID number 001 to migration ID number 002 via image ID #5 and image ID #7.

Figure 7:
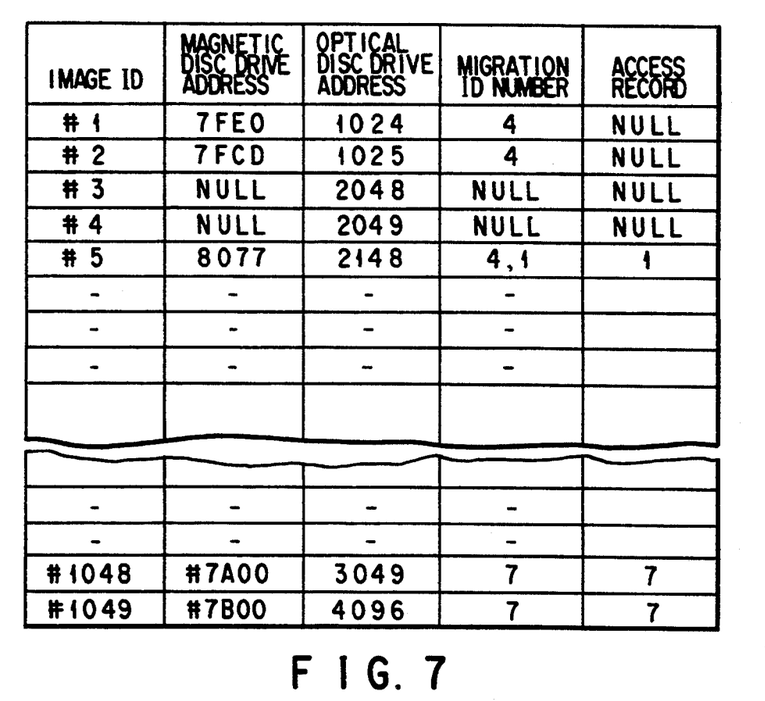
FIG. 7 shows an address management table according the embodiment.

FIG. 7 shows an example of the address management table 356B. The table 356B can record a storage address in the magnetic disc drive 320 for each image, a storage address in the optical disc drive 312 for each image, a migration ID number for each image, and the occurrence of access (access record) for each image. Since the contents of this table are fixed-length data, this table can be realized by using a fixed-length file.

For example, in FIG. 7, the image of image ID #2 is stored at address 7FCD of the magnetic disc drive 320 and at address 1025 of the optical disc drive 312, and it is migrated at migration ID number 4. The access record is "NULL", which means that an access or transfer of data to the work station 400 has been performed.

In FIG. 7, the image of image ID #5 is migrated at two migration ID numbers 4 and 1. The access record is "1", which means that the image of image ID #5 has been accessed or transferred to migration ID number 1, but it has not been accessed to migration ID number 4. That is, transfer to the work station 400 is not finished. Thus, image ID #5 cannot be deleted. In addition, in FIG. 7, the image of image ID #1048 has been migrated by migration ID number 7 and accessed by migration ID number 7. Accordingly, the image of image ID #1048 is normally at top priority for deletion.

The operation of the PACS with the above structure will now be described.

Figure 8:
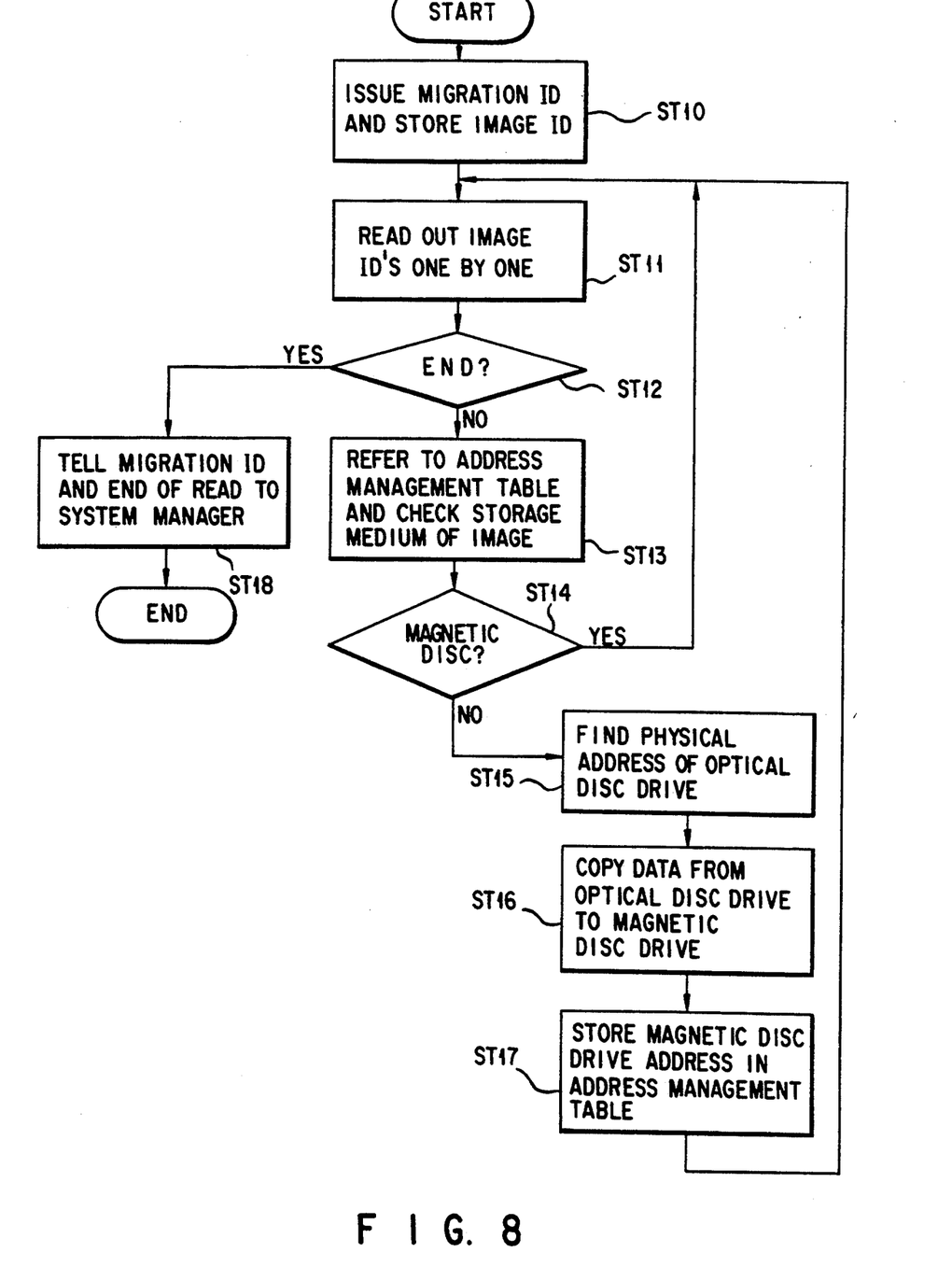
FIG. 8 is a flow chart illustrating the migration processing in the data base according to the embodiment.

When at least one image ID is sent to the data base 300 from the system manager 500, the CPU 352 of the system control 350 is activated and the migration processing, as shown in the flow chart of FIG. 8 is performed.

Referring to FIG. 8, when the migration processing is started, the migration ID number is issued from the migration ID issue unit 358 and the image ID is stored in the memory of the CPU 352 (step ST10). Image IDs stored in the memory of the CPU 352 are read out one by one (step ST11), and it is determined whether all desired image IDs have been read out (step ST12).

If "NO" in step ST12, the address management table 356B shown in FIG. 7 is referred, and a medium storing the image in question is checked (step ST13). Subsequently, it is determined whether the image is stored in the magnetic disc drive 320. If the image is in the magnetic disc drive 320, the control routine goes back to step ST11. If the image is not in the magnetic disc drive 320, the control routine goes to step ST15 (step ST14).

In step ST15, the optical disc file management unit 354 is accessed, and the physical address of the optical disc drive 312 is obtained. Image data corresponding to the optical disc drive 312 is read out, and the read-out image data is copied to the magnetic disc drive 320 (step ST16). In step ST17, the magnetic disc drive address corresponding to the image ID in the address management table 356B shown in FIG. 7 is rewritten from "NULL" to the address of the destination magnetic disc drive. The control routine returns to step ST11 and the next image ID is read out, thus performing the same processing as was described above.

If "YES" in step ST12, the migration ID and the end of read are told to the system manager 500 (step ST18). Then, the whole migration processing is completed.

Figure 9:
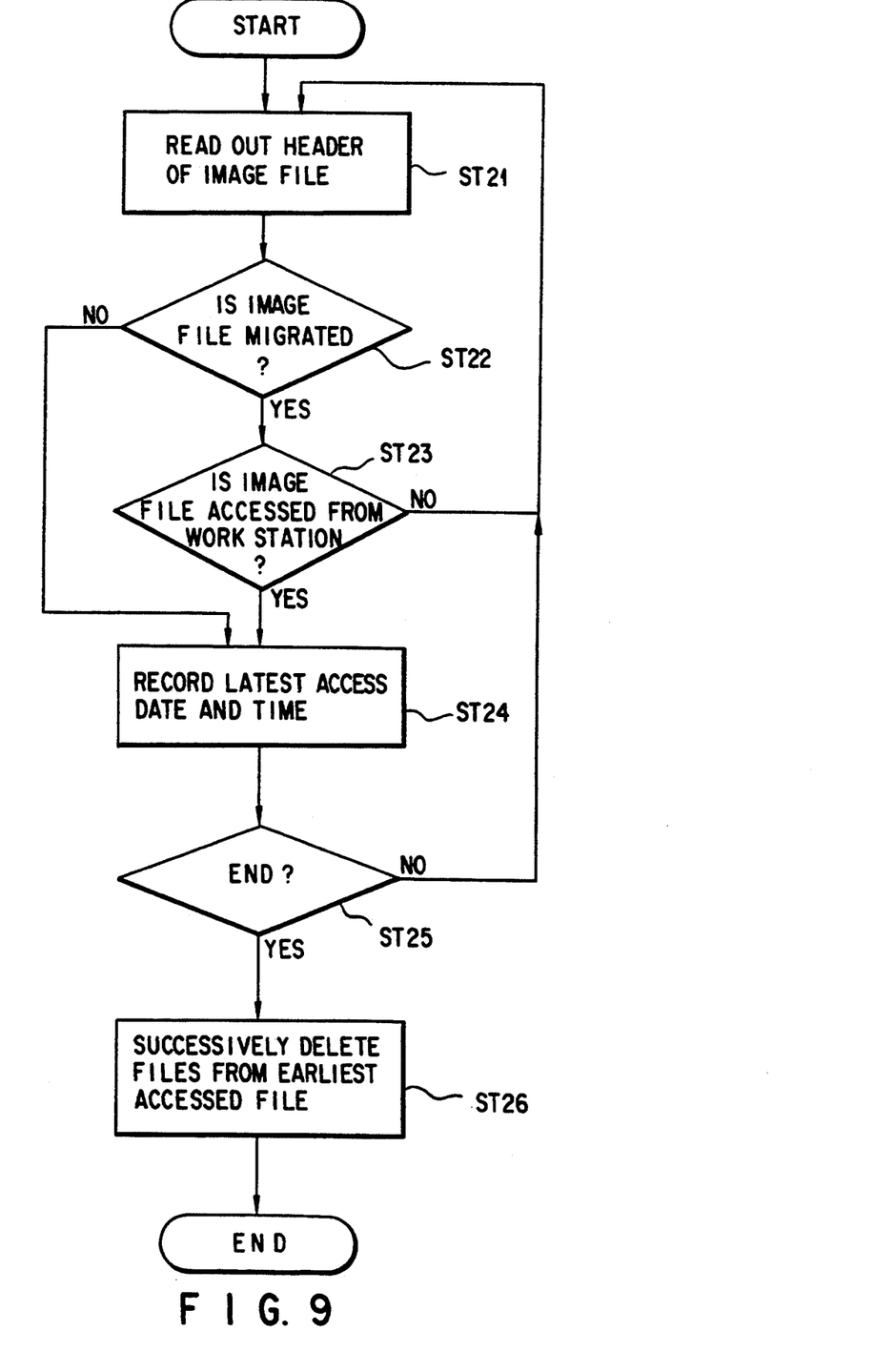
FIG. 9 is a flow chart illustrating the procedure for data deletion according to the embodiment and FIG. 10 illustrates the operation of the entire system in response to commands and requests according the embodiment.

The processing for deleting image data stored in the magnetic disc drive 320 will now be described with reference to the flow chart shown in FIG. 9.

When a program for deleting image data stored in the magnetic disc drive 320 is started, the header (address) of the image file stored in the magnetic disc is read out by referring to the address management table 356B (step ST21).

Whether the read-out image file has been migrated is determined on the basis of the migration ID number of the address management table 356B (step ST22). If "YES" in step ST22, it is determined whether the read-out image file has been accessed from the work station 400 on the basis of the access record in the address management table 356B (step ST23). If "NO" in step ST23, the control routine returns to step ST21. If "YES" in step ST23, the latest access date and time are recorded in the magnetic disc file management unit 356 (step ST24). If "NO" in step ST22, the control routine goes to step ST24 and the latest access date and time are recorded in the magnetic disc file management unit 356.

Once the latest access date and time have been recorded in the magnetic disc file management unit 356 in step ST24, it is determined whether the latest access date and time relating to all image data stored in the magnetic disc drive 320 have been recorded (step ST25). If "NO" in step ST25, the control routine returns to step ST21 and the header of the next image file is read out. If "YES" in step ST25, the files (image IDs) are successively deleted from the earliest accessed one (step ST26).

Figure 10:
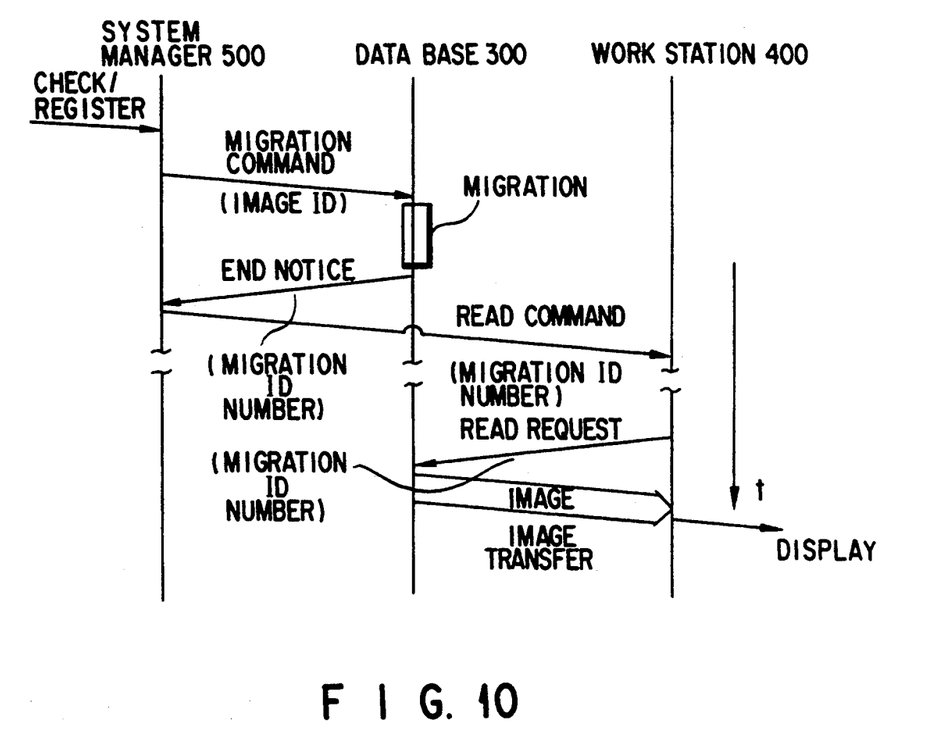

FIG. 10 is a view illustrating the entire operation of the PACS in the "migration processing" mode in the present invention.

When a migration command (image ID) is output from the system manager 500 to the data base 300, the data base 300 executes the above-described migration processing. Once the migration processing is completed, an end notice is sent to the system manager 500 (i.e. notice of migration ID number). A read command (migration ID number) is transmitted from the system manager 500 to the work station 400. Thereafter, a read request (migration ID number) is output from the work station 400 to the data base 300. Thus, image data accessed by the migration ID number is transferred from the data base 300 to the work station 400.

As has been described above, according to the apparatus of this embodiment, the magnetic disc file management unit 356 is provided with the migration management table 356A and address management table 356B. Thereby, the files in the magnetic disc drive 320 are managed.

Specifically, when the migration command is output from the system manager 500, the migration management table 356A records, in a linked manner, the ID number (migration ID number) unique to the system indicating the class of migration, which is issued from the migration ID issue unit 358 provided in the data base 300, and at least one image ID managed collectively by this migration ID number as header information of the image data stored in the magnetic disc drive 320. The address management table 356B comprises the image ID of image data written in the magnetic disc drive 320, physical address of the magnetic disc drive 320, physical address in the optical disc drive 312, migration ID number, and access record showing an access number (e.g. a flag) indicating the occurrence of access in the work station 400.

As has been described above, according to this invention, the migrated image data on the magnetic disc drive 320 is preferentially accessed by the management tables 356A and 356B of the magnetic disc file management unit 356 of the data base 300. Thus, data access can always be performed within a predetermined period. Since image IDs can be collectively managed by each migration ID number, the control of the overall system is easy. In addition, since the image data can be deleted from the earliest accessed file, by referring to the access record indicating the occurrence of access as header information of image data in the magnetic disc drive 320, it is possible to prevent non-accessed data from being erroneously deleted from the magnetic disc drive 320. The wait time until the transfer of desired image data can remarkably be reduced.

In the above embodiment, the data base 300 is provided with the migration ID issue unit 358 and the migration ID number is issued in response to the migration command from the system manager 500. However, it is possible that the system manager 500 issues the migration ID number beforehand and the migration ID number is delivered to the data base 300.

In the above embodiment, a single data base 300 is managed by migration IDs. However, it is possible to manage image data stored separately in two or more data bases 300 by a single migration ID.

In the above embodiment, the flag is written in the access record when the occurrence of access is recorded in the access record. However, if it is determined whether image data can be deleted, any recording method, other than use of the flag, is available. For example, in FIG. 7, image ID #5 is migrated by migration ID numbers 1 and 4 and the access record indicates the access of migration ID number 1. When the migration ID number 1 is accessed, it is possible to delete migration ID number 1 and retain migration ID number 4, while leaving the access record of "NULL". In this case, it is understood that the migration ID number 4 has not been accessed. Accordingly, the image data of the image ID, the migration ID number of which is "NULL", is an image to be deleted. In this case, the access record is not needed.

The above embodiment is directed to the case where migration management and address management of the image ID are performed. However, a check ID may be substituted for the image ID.

In the above embodiment, image IDs stored in the memory of the CPU are read out one by one. A plurality of image IDs may be read out all in one.

Additionally, in the above embodiment, the corresponding image IDs are migrated one by one. However, the migration may be performed per one diagnosis.

various changes and modifications may be made to the present invention without departing from the spirit of the invention.

Additional advantages and modifications will readily occur to those skilled in the art. Therefore the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A picture archiving communication system for medical application, comprising:
   at least one work station;
   a data base, including a low-speed recording medium and a high-speed recording medium, for storing image data collected by a diagnosing apparatus;
   means for reading out, when a transfer command for desired image data is sent from the work station to the data base, the image data from the image data registered in the data base and transfers the read-out image data to the work station;
   migration processing means for performing migration processing in which image data stored in the low-speed recording medium is copied to the high-speed recording medium in the data base;
   file management means connected to the migration processing means and including a management table for storing a migration index number generated by the file management means, said migration index number corresponding to at least one image data in the high-speed recording medium, said image data in the high-speed recording medium subjected to the migration processing and migrated by said migration processing means, and including a record generated by the file management means indicating whether the image data stored in the high-speed recording medium was accessed by said work station after the migration process; and
   data deleting means for determining whether at least one of the image data stored in the high-speed recording medium from the management table has been accessed, and, if a least one of the image data has been accessed, for deleting the image data from the high-speed recording medium from the accessed image data at an earliest time.

2. The system according to claim 1, further comprising migration index number issuing means for issuing the migration index number, wherein said file management means further includes an index file for receiving the migration index number for said migration index number issuing means, and for outputting to the management table the index number of the image data transferred to the working station in accordance with the migration index number.

3. A picture archiving communication system for medical application, comprising:
   at least one work station;
   a data base, including a low-speed recording medium and a high-speed recording medium, for storing image data collected by a diagnosing apparatus;
   means for reading out, when a transfer command for desired image data is sent from the work station to the data base, the image data from the image data registered in the data base and transfers the read-out image data to the work station;
   migration processing means for performing migration processing in which image data stored in the low-speed recording medium is copied to the high-speed recording medium in the data base;
   file management means connected to the migration processing means and including a management table for storing a migration index number generated by the file management means, said migration index number corresponding to at least one image data in the high-speed recording medium, said image data in the high-speed recording medium subjected to the migration processing and migrated by said migration processing means, and including a record generated by the file management means indicating whether the image data stored in the high-speed recording medium was accessed by said work station after the migration process; and
   data protecting means for determining whether the image data stored in the high-speed recording medium from the management table has been accessed, and, if the image data has not been accessed, protecting the image data so as not to be deleted.

4. A picture archiving communication system for medical application, comprising:
   at least one work station;

a data base, including a low-speed recording medium and a high-speed recording medium, for storing image data collected by a diagnosing apparatus;

means for reading out, when a transfer command for desired image data is sent from the work station to the data base, the image data from the image data registered in the data base and transfers the read-out image data to the work station;

migration processing means for performing migration processing in which image data stored in the low-speed recording medium is copied to the high-speed recording medium in the data base;

means for outputting any one of a migration index number, an image index and a data index in response to a migration command from the migration processing means; and file management means including an index file which receives one of the image index and the data index, and refers to at least one of a physical address in the low-speed recording medium and a physical address in the high-speed recording medium.

5. The system according to claim 4, wherein said file management means includes a management table for storing a migration index number corresponding to at least one image data in the high-speed recording medium which was subjected to the migration processing migrated by said migration processing means, and a record indicating whether the image data stored in the high-speed recording medium was accessed after the migration processing.

6. The system according to claim 5, further comprising data deleting means for determining whether the image data stored in the high-speed recording medium from the management table has been accessed, and, if the image data has been accessed, for deleting the image data corresponding to the image data earliest accessed from the high-speed recording medium.

7. A picture archiving communication system operated from a work station by an operator for medical application, comprising:

a data base, including a low-speed recording medium and a high-speed recording medium, for storing image data collected by a diagnosing apparatus;

processor means for reading out operator selected image data corresponding to a particular image from the low-speed recording medium and the high-speed recording medium to the work station, and for determining in advance the operator selected image data, the processor means assigning an image index number for said determined in advance operator selected image data;

migration processing means for automatically copying said determined in advance operator selected image data from the low-speed recording medium to the high-speed recording medium, such that the determined in advance operator selected image data is available to the operator in high-speed memory;

file management means including a migration management table, an address management table, and an migration index number issuing means, wherein the migration index number issuing means issues a migration index number corresponding to each migration when the migration processing means copies image data to the high-speed recording means, and wherein the migration management table stores each said migration index number and stores all said determined in advance operator selected image data for a corresponding said migration, each said migration index number linked in the migration management table to said determined in advance operator selected image data of each said corresponding migration, and wherein the file management means constructs and updates the address management table from the migration management table, the address management table organized by said image index number, and wherein each said image index number in said address management table being linked with a low-speed recording medium address, a high-speed recording medium address, the migration index number in which corresponding image data had migrated, and an access record which records each said migration index number in which corresponding image data and said image index number is accessed by the operator; and deleting means for deleting from said high-speed recording means image data corresponding to one of said image index number when a corresponding said access record lists all migration index numbers which are listed in the migration index number.

* * * * *